United States Patent [19]
Toukan et al.

[11] 3,933,819
[45] Jan. 20, 1976

[54] FLUORINATED AROMATIC AND HETEROCYCLIC SULFIDES

[75] Inventors: Sameeh Said Toukan, Phoenixville; Murray Hauptschein, Glenside, both of Pa.

[73] Assignee: Pennwalt Corporation, Philadelphia, Pa.

[22] Filed: Sept. 12, 1973

[21] Appl. No.: 396,649

Related U.S. Application Data

[63] Continuation-in-part of Ser. No. 171,325, Aug. 21, 1971.

[52] U.S. Cl.......... 260/251; 260/307 R; 260/268 R; 260/309.2; 260/306; 260/289 R; 260/516; 260/579; 260/307 D; 260/256.5 R

[51] Int. Cl.$^2$.................................. C07D 239/00
[58] Field of Search .................................. 260/251

[56] References Cited
UNITED STATES PATENTS 3,172,910  3/1965  Brace ............................. 260/539

*Primary Examiner*—Elbert L. Roberto

[57] ABSTRACT

Fluorinated-alkyl sulfides represented by $[R_f(CH_2)_nS]_zQ$ where $R_f$ is fluoroalkyl, $n$ is 2 or 3, $z$ is 1 or 2, and Q is an aryl, alkylaryl, alkyl heterocyclic or heterocyclic radical, are useful as surfactants or as intermediates for the preparation of salt-type, quaternary-salt, or amphoteric surfactants.

6 Claims, No Drawings

FLUORINATED AROMATIC AND HETEROCYCLIC SULFIDES

This application is a continuation-in-part of Ser. No. 171,325, filed Aug. 21, 1971.

This invention concerns novel fluorinated-alkyl sulfides containing aromatic and heterocyclic moieties. More particularly, this invention is directed to fluorinated alkyl sulfides represented by $[R_f(CH_2)_nS]_zQ$ where $R_f$ is a radical selected from the group consisting of perfluoroalkyl, perfluoroisoalkoxyalkyl and perfluoromonochloroalkyl radicals having from 5 to 13 carbon atoms, preferably from 7 to 11 carbon atoms, $n$ is 2 or 3, $z$ is 1 or 2, Q is an aryl, alkylaryl (i.e., lower alkyl), alkylheterocyclic (i.e., lower alkyl, e.g., 1 to 4 carbon atoms), or heterocyclic group having up to 14 ring-carbon atoms. A perfluoroalkyl radical is defined as one containing only carbon and fluorine; a perfluoroisoalkoxyalkyl radical contains only carbon, fluorine, and an oxygen in an ether linkage; a perfluoromonochloroalkyl radical is one which contains only fluorine, chlorine and carbon; any of the foregoing radicals may be straight chain or branched chain. The preferred $R_f$ radical is perfluoroalkyl. Representative $R_f$ radicals are, for example, $(CF_3)_2CF(CF_2CF_2)^-$
$(CF_3)_2CF(CF_2CF_2)_3^-$
$C_7F_{15}^-$
$C_{11}F_{23}^-$
$(CF_3)_2CFO(CF_2CF_2)^-$
$(CF_3)_2CFO(CF_2CF_2)_4^-$
$(CF_3)(CF_2Cl)CF(CF_2CF_2)^-$
$C_7ClF_{14}^-$
$C_8F_{17}^-$
$CF_2Cl(CF_2)_{10}^-$
$C_9F_{19}^-$
$C_{10}F_{21}^-$
$C_{13}F_{27}^-$ Q is an aryl, alkylaryl, or alkylheterocyclic, or heterocyclic group (i.e., heterocyclic means containing nitrogen, oxygen or sulfur atoms, or combinations thereof, in the organic ring). Such Q groups are exemplified by phenyl, naphthyl, pyridyl, pyrimidyl, thiazolyl, thiadiazolyl, oxazolyl, triazinyl, piperazinyl, piperidinyl, benzimidazolyl, benzothiozolyl, quinolinyl, furfuryl, thienyl and others of this class. In addition, such aryl, alkylaryl, alkylheterocyclic, or heterocyclic groups can optionally contain substituents such as

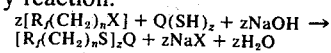

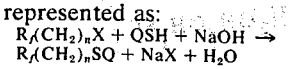

(where R and R' are independently hydrogen or lower alkyl).

In preparing the compounds of this invention, a fluoroalkylalkylene halide is reacted with a mercaptan in the presence of a basic substance, such as NaOH, to produce the sulfide products according to the exemplary reaction:

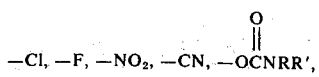

where $n = 2$ or 3, $z$ can vary from 1 to 2, X is Br or I, and $R_f$ and Q are as defined earlier.

In the case of mercaptan reactants having a single -SH group (i.e., $z = 1$), the reaction may be more simply represented as:

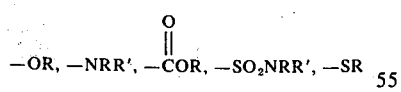

Representative mercaptan reactants are

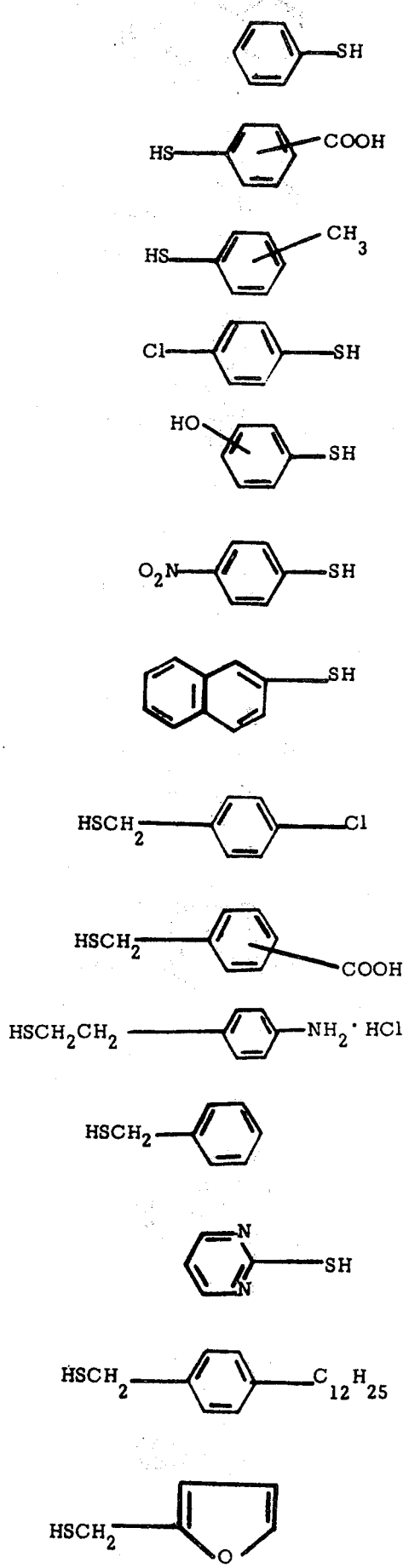

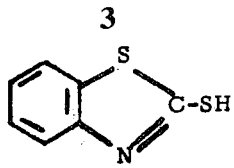

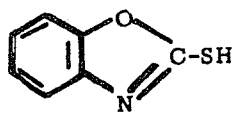

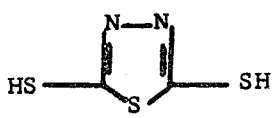

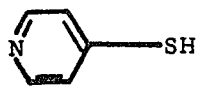

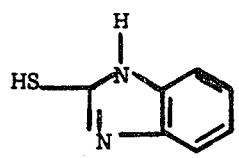

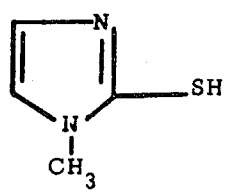

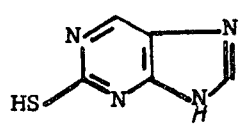

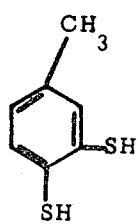

Among the basic materials that may be used in the abovedescribed reaction are alkali metal hydroxides, e.g., KOH and LiOH, and preferably NaOH, and such basic substances as triethylamine, sodium methoxide, potassium tert.-butoxide, and the like substances. The reaction is carried out by bringing the above-described reactants together at a temperature within the range of about 50° to about 150°C., preferably about 80° to 100°C. The reaction is normally carried out under atmospheric pressure. Reaction periods ranging from 1 to 24 hours are usually adequate, with from about 2 to 6 hours normally satisfactory.

The reaction preferably is conducted with the reactants in admixture in medium comprising organic polar liquid, which shows solvency for the fluoroalkylethylene halide, for example, methanol, ethanol, n-propanol, iso-propanol, n-amyl alcohol, n-hexanol, n-octanol, sec-butanol, n-butanol, isobutanol, tert-butanol, isoamyl alcohol, tert-amyl alcohol, 2-pentanol, cyclohexanol, 2-ethyl-1-hexanol and mixtures of said liquids. The weight ratio of polar solvent to fluoroalkylethylene halide will generally be in the range of about 2:1 to about 10:1. In the more preferred embodiments the solvent is essentially anhydrous.

The sulfides of this invention are selectively useful as surface tension depressants of organic and aqueous systems, and the acid-salt, quaternary-salt and amphoteric derivatives of the sulfides where Q is a heterocyclic nitrogen-containing moiety (e.g., pyridyl, piperidinyl, etc.) are especially superior surfactants due to their excellent ability to lower surface tensions in aqueous systems. Amphoteric surfactants are prepared by reacting the appropriate sulfide with such reactants as monochloroacetic acid, monobromoacetic acid, beta-propiolactone, propanesultone, alkylene sulfites, and the like according to the representative reactions:

I.

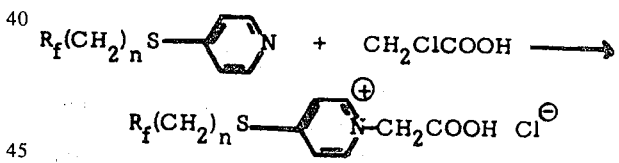

II.

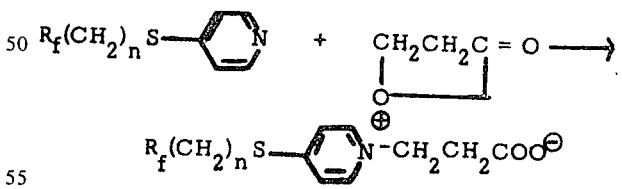

III.

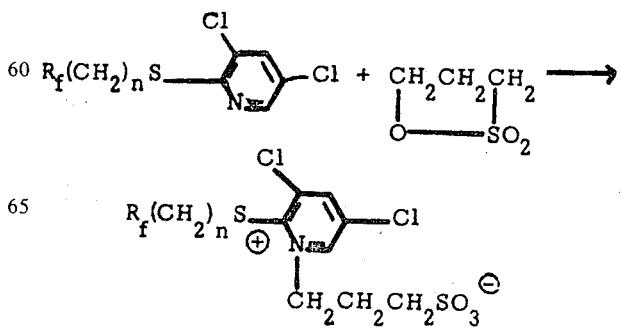

Quaternary salts are prepared by reacting the heterocyclic nitrogen-containing sulfide with a lower alkyl halide quaternizing agent ($R_qX$, where $R_q$ is lower alkyl and X is iodine, or less preferably bromine), for example, in a solvent such as diethyl ether or ethanol, or with dimethyl sulfate. Acid salt derivatives are readily prepared from the nitrogen-containing sulfides by reaction with acids such as HCl, $H_2SO_4$, acetic acid and the like.

Compounds embodied herein may also be used to kill or inhibit the growth of bacterial microorganisms, including staphylococcus aureus and aspergillus niger.

In the following examples, which illustrate and clarify the present invention, the infrared spectrum of each synthesized product is consistent with the structure set forth.

EXAMPLE 1

Preparation of

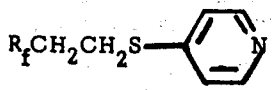

A solution of 6.7 g (0.06 mole) of 4-mercaptopyridine and 2.4 g. (0.06 mole) of NaOH in 35 ml. EtOH is heated for 10–15 minutes to 40°–50°C. The resulting brown mixture is cooled and then added slowly at ambient temperature to a solution of 31.5 g. (0.06 mole) of $(CF_3)_2CF(CF_2)_4CH_2CH_2I$ in 100 ml. tert-amyl alcohol. The mixture is refluxed for 24 hours, filtered to remove a very small amount of insoluble material, and the filtrate is stripped of solvent at 40°–50°C. to leave 65.0 g. of light brown residue. This residue is in turn extracted with 5 × 100 ml. portions of hot ether and the ether extract washed with 100 ml. water, 100 ml. 5% NaOH, and 100 ml. water, then dried and heated on a steam bath to remove solvent. The brown liquid residue is distilled to afford 23.8 g. (78% yield) of light brown liquid product b.p. 101°C. (0.08 mm.) $n_D^{25.2}$, 1.4127. Upon standing at room temperature, the product,

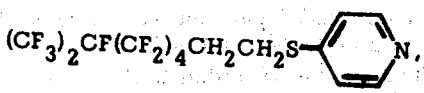

becomes crystalline, m.p. 34°–36°C.

Analysis. - Calcd. for $C_{14}H_8F_{15}NS$: C, 33.15%; H, 1.59%; N, 2.76%. Found: C, 33.36%; H, 1.82%; N, 2.92%.

Preparation of Heterocyclic Amphoteric Surfactant

A mixture of 0.01 mole of the above-prepared product and 0.01 mole of monochloroacetic acid is heated slowly to 125°–130°C. with occasional shaking in an oil bath, at which point the heat is turned off and the reaction mixture kept in the oil bath while the temperature slowly falls to 30°C. There is obtained in 100% yield the amphoteric surfactant

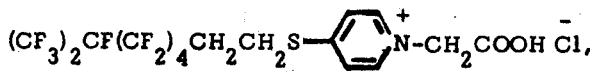

a light brown solid, m.p. 178°C.

Analysis. - Calcd. for $C_{16}H_{11}ClF_{15}NO_2S$: C, 31.93%; H, 1.85%; Cl, 5.89%; N, 2.33%. Found: C, 31.83%; H, 2.17%; Cl, 5.90%; N, 2.46%.

| Surface Tension of Aqueous Solutions of the Heterocyclic Amphoteric Surfactant | |
|---|---|
| Concentration | Dynes/cm at 25°C. |
| 0.01% | 18 |
| 0.001% | 32 |

The unpredictable and exceptional performance of this heterocyclic amphoteric surfactant is even more impressive when it is compared to that of the only commercially available fluorinated amphoteric, the aliphatic $C_8F_{17}SO_2NH(CH_2)_3N^+(CH_3)_2CH_2CH_2COO^-$, which has the following surface activity

| Concentration | Dynes/cm at 25°C. |
|---|---|
| 0.1% | 19 |
| 0.01% | 27 |
| 0.001% | 40 | and which has a longer chain length in the expensive fluorocarbon portion.

The performance of the heterocyclic amphoteric also compares favorably with the performance of the aliphatic surfactants disclosed in Hager and Walter's application, Ser. No. 145,556, filed May 20, 1971, and the instant compounds advantageously do not contain hydrolyzable ester or amide linkages.

In addition, the heterocyclic surfactant inhibits the growth of *Staphylococcus aureus* and *Aspergillus niger* at a concentration of about 500 ppm.

EXAMPLE 2

Preparation of

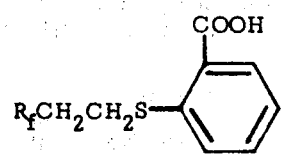

Using the procedure of Example 1, o-mercaptobenzoic acid is reacted with $(CF_3)_2CF(CF_2)_4CH_2CH_2I$ to produce, in 64% yield, the white solid product

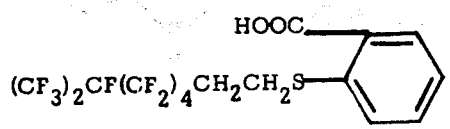

m.p. 114°–116°.

Analysis. - Calcd. for $C_{16}H_9F_{15}O_2S$: C, 34.93%; H, 1.65%; S, 5.83%. Found: C, 35.24%; H, 1.77%; S, 5.61%.

The compound inhibits the growth of *Staphylococcus aureus* (ATCC 6438) when used at a concentration of 1000 ppm.

The surface tension of a 0.1% aqueous solution of the sodium salt of the compound is 17 dynes/cm. at 25°C., again an unexpectedly exceptional performance when compared with that of a superficially similar aliphatic compound $(CF_3)_2CF(CF_2)_4CH_2CH_2SCH_2CH_2COONa$ (prepared via reaction of 3-mercaptopropionic acid with $C_9F_{19}C_2H_4I$ in tert.-amyl alcohol) which produces a surface tension in 0.1% aqueous solution of 21 dynes/cm. at 25°C.

Similar low surface tensions are obtained with other alkali metal salts in accordance with the compound of this example, e.g., potassium, ammonium and substituted ammonium salts, i.e., anionic surfactant compounds represented by the structure

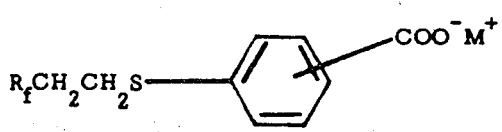

where M is alkali metal, ammonium, or substituted ammonium.

EXAMPLE 3

Preparation of

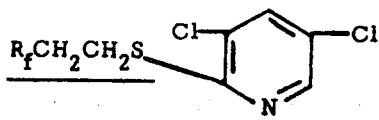

Following the procedure of Example 1, there is obtained a light green oily liquid,

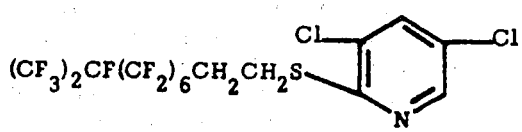

which partially solidifies on long standing at room temperature, b.p. 170°C. (2.8 mm.), $n_D^{25.8}$, 1.4014.

Analysis - Calcd. for $C_{16}H_6Cl_2F_{19}NS$: C, 28.42%; H, 0.90%, N, 2.07%. Found: C, 27.91%, H, 1.06%; N, 1.75%.

EXAMPLE 4

Preparation of

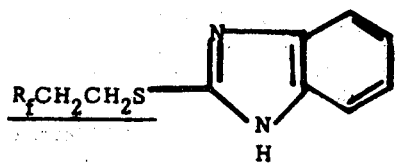

A solution of 9.0 g. (0.06 mole) of 2-benzimidazolethiol and 2.4 g. (0.06 mole) of NaOH in 35 ml. abs. ethanol is heated for 15 minutes to 40°–50°C. The resulting brown mixture is cooled and added slowly to a water-cooled solution of 31.5 g. (0.06 mole) of $(CF_3)_2CF(CF_2)_4CH_2CH_2I$ in 100 ml. tert-amyl alcohol. The mixture is refluxed for 19 hours, and worked-up as in Example 1. The crude product is recrystallized from 50 ml. 80% ethanol to afford 23.2 g. (71% yield) of light brown solid,

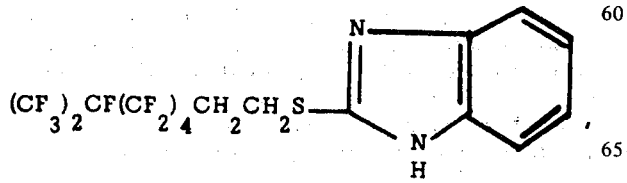

m.p. 115°–119°C.

Analysis. - Calcd. for $C_{16}H_9F_{15}N_2S$: C, 35.18%; H, 1.66%; N, 5.13%. Found: C, 35.34%; H, 1.93%; N, 5.15%

The compound inhibits growth of *Aspergillus niger* at a concentration of 1,000 ppm.

EXAMPLE 5

Preparation of

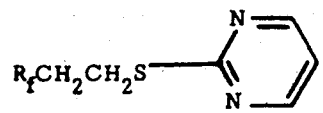

Following the procedure of Example 4, a mixture of 0.06 mole of $(CF_3)_2CF(CF_2)_4CH_2CH_2I$, 0.06 mole of 2-mercaptopyrimidine, and 0.06 mole of NaOH in 40 ml. abs. ethanol and 100 ml. tert-amyl alcohol is refluxed to produce a light green liquid product (84% yield),

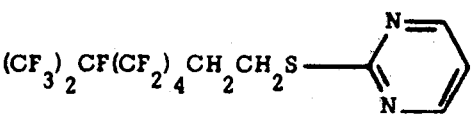

b.p. 128° (3 mm.), $n_D^{29.7}$, 1.4007.

Analysis: - Calcd. for $C_{13}H_7F_{15}N_2S$: C, 30.72%; H, 1.39%; N, 5.51%. Found: C, 30.82%; H, 1.72%; N, 5.10%.

The compound inhibits growth of *Aspergillus niger* when used at a concentration of 1000 ppm.

We claim:
1. A fluorinated alkyl sulfide compound represented by the structure $[R_f(CH_2)_nS]_zQ$ where $R_f$ is selected from the class consisting of perfluoroalkyl, perfluoroisoalkoxyalkyl and perfluoromonochloroalkyl radicals having from 5 to 13 carbon atoms, Q is selected from the group consisting of pyridyl, pyrimidyl, triazinyl, piperazinyl, piperidinyl and quinolinyl, n is an integer of 2 or 3, and z is 1 or 2.
2. The compound according to claim 1 wherein n is 2 and z is 1.
3. The compound according to claim 2 wherein $R_f$ has from 7 to 11 carbon atoms.
4. The compound according to claim 2 wherein $R_f$ is perfluoroalkyl.
5. A compound according to claim 4 wherein Q is

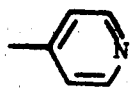

6. A compound according to claim 4 wherein Q is

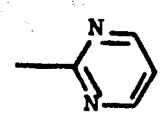

* * * * *